(12) United States Patent
Tipler et al.

(10) Patent No.: US 6,652,625 B1
(45) Date of Patent: Nov. 25, 2003

(54) ANALYTE PRE-CONCENTRATOR FOR GAS CHROMATOGRAPHY

(75) Inventors: Andrew Tipler, Trumbull, CT (US); Gary Campbell, New Milford, CT (US); Mark Collins, Huntington, CT (US)

(73) Assignee: Perkin Elmer Instruments LLC, Shelton, CT (US)

( * ) Notice: Subject to any disclaimer, the term of this patent is extended or adjusted under 35 U.S.C. 154(b) by 0 days.

(21) Appl. No.: 10/202,147

(22) Filed: Jul. 24, 2002

(51) Int. Cl.⁷ .............................................. B01D 15/08
(52) U.S. Cl. ............................ 95/82; 73/23.41; 96/105
(58) Field of Search ................... 95/82, 86, 87, 95/89; 96/101, 104, 105; 73/23.35, 23.41

(56) References Cited

U.S. PATENT DOCUMENTS

| | | | |
|---|---|---|---|
| 2,813,010 A | | 11/1957 | Hutchins |
| 3,999,963 A | | 12/1976 | Ririe |
| 4,038,053 A | | 7/1977 | Golay |
| 4,245,494 A | | 1/1981 | Legendre et al. |
| 4,293,316 A | | 10/1981 | Block |
| 4,805,441 A | * | 2/1989 | Sides et al. ................ 73/23.25 |
| 4,849,179 A | * | 7/1989 | Reinhardt et al. ............ 422/89 |
| 5,347,844 A | * | 9/1994 | Grob et al. ................ 73/23.41 |
| 5,545,252 A | | 8/1996 | Hinshaw et al. |
| 5,612,225 A | | 3/1997 | Baccanti et al. |
| 5,711,786 A | | 1/1998 | Hinshaw |
| 5,759,234 A | * | 6/1998 | Munari et al. ................. 95/14 |
| 5,814,128 A | | 9/1998 | Jiang et al. |
| 5,929,321 A | * | 7/1999 | Bertrand ................... 73/23.39 |
| 5,944,877 A | * | 8/1999 | O'Neil ........................ 96/101 |
| 5,954,862 A | * | 9/1999 | Wilson ........................ 96/101 |
| 6,093,371 A | * | 7/2000 | Wilson ........................ 422/89 |
| 6,148,657 A | * | 11/2000 | Satoh et al. ............... 73/23.35 |
| 6,223,584 B1 | | 5/2001 | Mustacich et al. |

FOREIGN PATENT DOCUMENTS

DE            41 19 453           6/1991

* cited by examiner

Primary Examiner—Robert H. Spitzer
(74) Attorney, Agent, or Firm—St. Onge Steward Johnston & Reens LLC

(57) ABSTRACT

An analyte pre-concentrator for gas chromatography is disclosed generally comprising a tube having a restricted outlet and packed with an adsorbent, wherein the tube serves as the liner of a chromatographic injector, as an adsorbent trap coupled to a chromatographic column, and/or as an adsorbent trap coupled to a headspace sampler. Preferably, a heating device allows the tube to be heated. In a preferred embodiment, the analyte pre-concentrator further comprises a column isolating accessory so that a chromatographic column can be temporarily isolated from substances flowing through the tube.

37 Claims, 9 Drawing Sheets

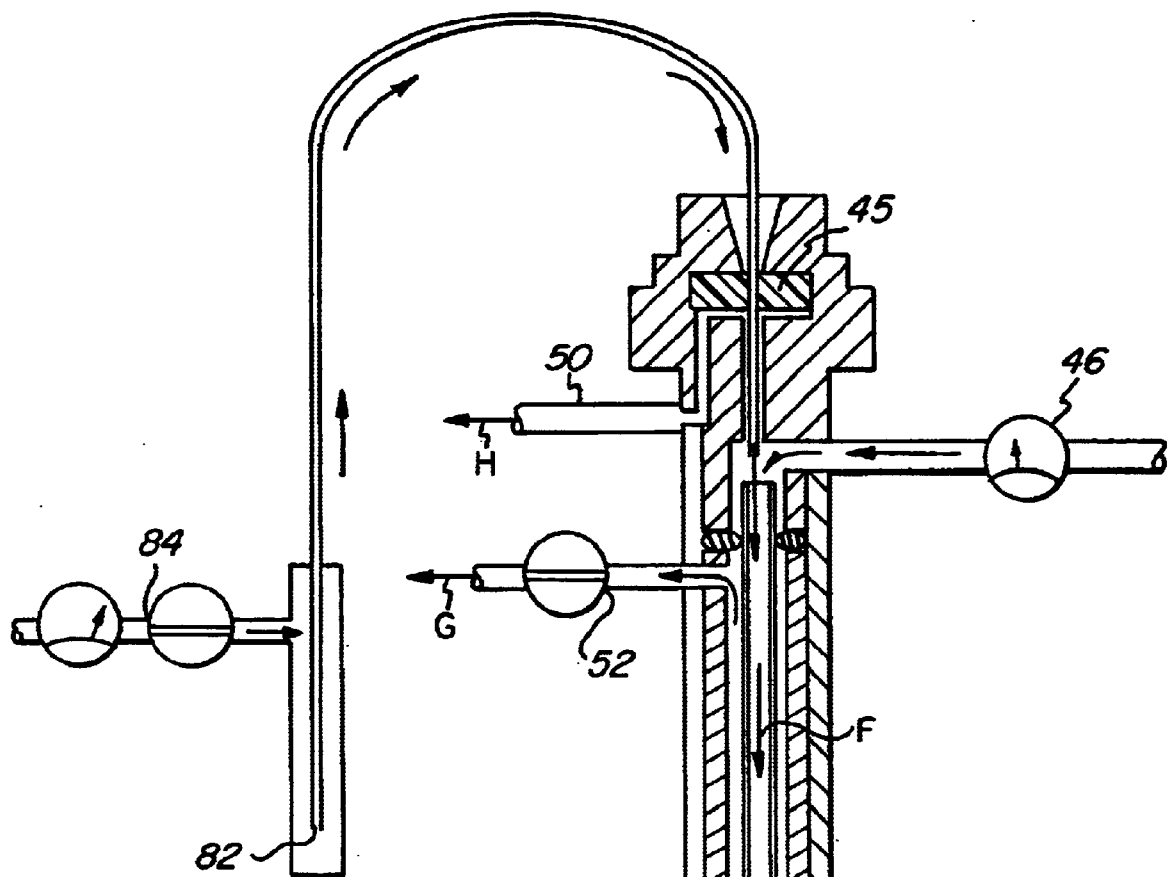
FIG. 9
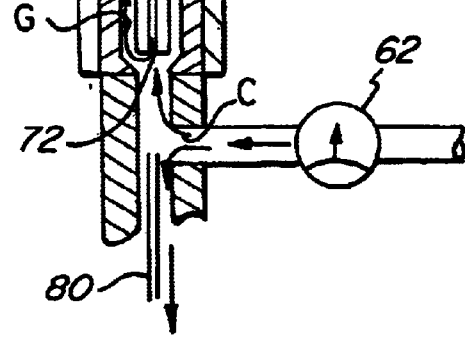

ANALYTE PRE-CONCENTRATOR FOR GAS CHROMATOGRAPHY

FIELD OF THE INVENTION

The present invention relates to a method and apparatus for pre-concentrating analytes and removing moisture in a sample. More specifically, the invention relates to an adsorbent trap for use with chromatographic columns, chromatographic injectors, and headspace samplers.

BACKGROUND OF THE INVENTION

Chromatography is essentially a physical method of separation in which constituents of a test sample in a carrier gas or liquid are adsorbed or absorbed and then desorbed by a stationary phase material in a column. A pulse of the sample is introduced into a steady flow of carrier gas. At the end of the column, the individual components are more or less separated in time. Detection of the gas provides a time-scaled pattern that, by calibration or comparison with known samples, indicates the constituents of the test sample. An example of the process by which this occurs is described in U.S. Pat. No. 5,545,252 to Hinshaw.

The value of using a separate, heated device for receiving the sample and subsequently introducing it into the column has long been recognized. One such device is disclosed in U.S. Pat. No. 4,038,053 to Golay, which describes using a chromatographic injector for receiving the sample, heating it, and subsequently injecting it into a chromatographic column. Such a device is desired because higher sample equilibrium temperatures can result in much larger chromatographic peaks. A disadvantage of such devices, however, is that such temperature increases may also increase the concentration of other material that detrimentally affects the sensitivity of the system, such as water.

To remedy this problem, numerous assemblies have been suggested to pre-concentrate analytes in a sample and remove moisture therefrom prior to introducing the sample into a chromatographic column. For example, U.S. Pat. No. 5,612,225 to Beccanti, U.S. Pat. No. 4,245,494 to Legendre, and U.S. Pat. No. 2,813,010 to Hutchins disclose a means for removing water from a sample prior to introducing the sample into a chromatographic column by first passing the sample through an anhydrous substance, which absorbs the water. However, because the anhydrous substance absorbs the water, rather than adsorbing the analyte and allowing the water to be purged from the system, repeated use of the anhydrous substance is likely to be limited and require frequent replacement.

Several assemblies have been suggested which utilize an adsorbent trap, which adsorbs the analytes while allowing water to pass through. For example, U.S. Pat. No. 6,223,584 to Mustacich discloses the use of an adsorbent trap in a pre-concentrator assembly for pre-concentrating analytes in a sample prior to introducing the sample into a chromatographic column, which device comprises a tube containing an adsorbent material. However, a disadvantage of this arrangement is the dead volume that exists between the adsorbent bed and the chromatographic column, which is undesirable because, at typical column flow rates, excessive peak broadening results.

U.S. Pat. No. 5,814,128 to Jiang discloses the use of an adsorbent trap in conjunction with a separate water management device, which device removes water from a sample prior to entry into a chromatographic column via the swirling motion caused by a threaded (or other non-smooth geometrically shaped) bore in the device. Similarly, U.S. Pat. No. 4,293,316 to Block discloses the use of an adsorbent trap in conjunction with a membrane separator device, which device removes water from a sample prior to entry into a gas analyzer. However, rather than optimizing the utility of the adsorbent trap itself as a means for analyte pre-concentration and moisture elimination, these assemblies each require a separate device in addition to the trap, which not only creates additional manufacture and maintenance costs, but also does not solve the aforementioned problem of excessive volume between the adsorbent bed and the chromatographic column.

One means of introducing a sample containing an analyte into a chromatographic column is known as "headspace sampling." In conventional headspace sampling, sample material is sealed in a vial and subjected to constant temperature conditions for a specified time. Analyte concentrations in the vial gas phase should reach equilibrium with the liquid and/or solid phases during this thermostatting time. The vial is subsequently pressurized with carrier gas to a level greater than the "natural" internal pressure resulting from thermostatting and equilibration. Then the pressurized vial is connected to the chromatographic column in such a way as to allow for the transfer of a portion of the vial gas phase into the column for a short period of time. Such a system is disclosed in U.S. Pat. No. 5,711,786 to Hinshaw, which describes using a chromatographic injector between the vial and the chromatographic column. However, the use of such devices presently known in the art, including chromatographic injectors, for headspace applications results in the same disadvantages previously mentioned for introducing samples into chromatographic columns generally.

What is desired, therefore, is a method and apparatus for pre-concentrating analytes and eliminating moisture in a sample prior to introducing the sample into a chromatographic column. What is further desired is a method and apparatus for pre-concentrating analytes and eliminating moisture in a sample in a chromatographic injector. What is also desired is a method and apparatus for pre-concentrating analytes and eliminating moisture in a sample in connection with a headspace sampler.

SUMMARY OF THE INVENTION

Accordingly, an object of the present invention is to provide an analyte pre-concentrator for gas chromatography that permits temperature increases without detrimentally affecting the sensitivity of the chromatographic system.

It is a further object of the present invention to provide an analyte pre-concentrator for gas chromatography that provides a moisture trap permitting moisture to be purged from the chromatographic system so that the trap may be used for multiple injections.

It is yet another object of the present invention to provide an analyte pre-concentrator for gas chromatography that provides a moisture trap resulting in little or no dead volume between the trap and a chromatographic column, thereby decreasing excessive peak broadening.

It is still another object of the present invention to provide an analyte pre-concentrator for gas chromatography that provides a moisture trap without the addition of a separate device, thereby decreasing manufacturing and maintenance costs.

It is still another object of the present invention to provide a method for pre-concentrating analytes in a gas chromatographic system that achieves the objects listed above.

To overcome the deficiencies of the prior art and to achieve at least some of the objects and advantages listed, the invention comprises a chromatographic injector, a liner located inside the injector, the liner having an inlet and an outlet, wherein the inner diameter of the outlet is smaller than the inner diameter of the inlet, and an adsorbent located inside the liner. Preferably, the injector is temperature controllable.

In another embodiment, the invention comprises a tube having an inlet and an outlet, wherein the inner diameter of the outlet is smaller than the inner diameter of the inlet, an adsorbent located inside the tube, and a gas chromatographic column coupled to the tube. Preferably, the invention further comprises a heating device for heating the tube.

In another embodiment, the invention comprises a headspace sampler, a tube coupled to the headspace sampler, the tube having an inlet and an outlet, wherein the inner diameter of the outlet is smaller than the inner diameter of the inlet, and an adsorbent located inside the tube. Preferably, the invention further comprises a heating device for heating the tube.

In a preferred embodiment, the invention further comprises a column isolating accessory, with which a chromatographic column can be temporarily isolated from the tube or liner.

The invention also relates to a method comprising the steps of setting the pressures of a main carrier gas inlet and an auxiliary carrier gas inlet such that a column is isolated from substances flowing through a tube, introducing a sample mixture into the tube, such that the mixture passes through an adsorbent, which adsorbs the analytes, and is vented from the chromatographic system, introducing additional carrier gas into the tube, such that moisture is dry purged from the adsorbent, setting the pressures of the main carrier gas inlet and the auxiliary carrier gas inlet such that the column is no longer isolated from substances flowing through the tube, and heating the tube, such that the analytes adsorbed by the adsorbent are desorbed into the column.

The invention and its particular features will become more apparent from the following detailed description when considered with reference to the accompanying drawings.

BRIEF DESCRIPTION OF THE DRAWINGS

FIG. 9 is an exposed side view of the gas chromatographic system of FIG. 1 during the dry purge stage.

DETAILED DESCRIPTION OF THE INVENTION

Figure 1:
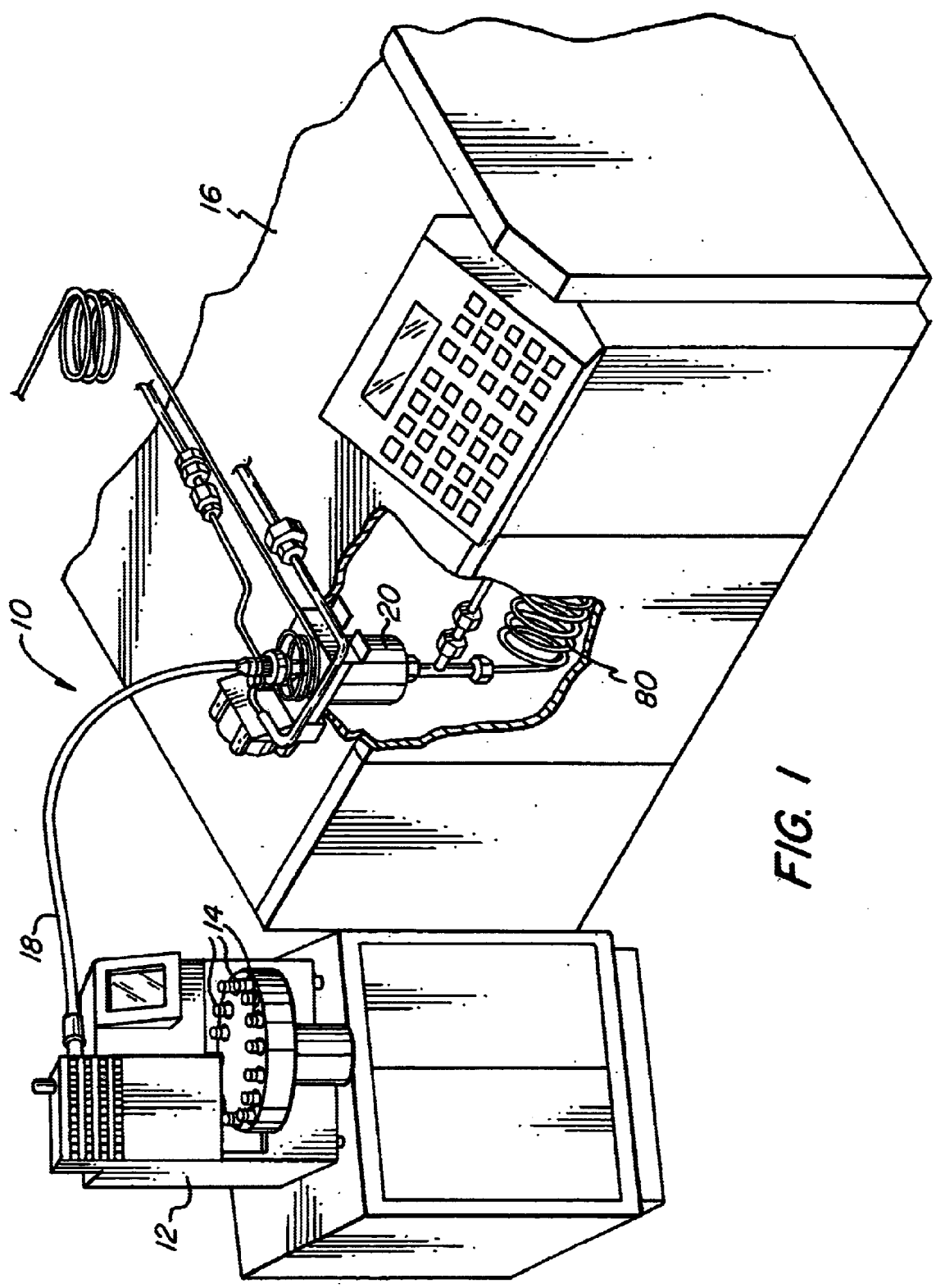
FIG. 1 is a perspective view of a gas chromatographic sampling system including a headspace sampler and a gas chromatograph in accordance with the invention.

The basic components of one embodiment of a gas chromatographic sampling system 10 in accordance with the invention are illustrated in FIG. 1. As used in this description, the terms "top," "bottom," "upper," and "lower" refer to the objects referenced when in the orientation illustrated in the drawings, which orientation is not necessary for achieving the objects of the invention.

In the embodiment depicted in FIG. 1, a headspace sampler 12 holds a plurality of vials 14 that contain the sample to be analyzed. The headspace sampler 12 is connected to a gas chromatograph 16 via a transfer line 18. The basic components of the gas chromatograph are an injector 20, a chromatographic column 80, and a detector (not shown).

Figure 2:
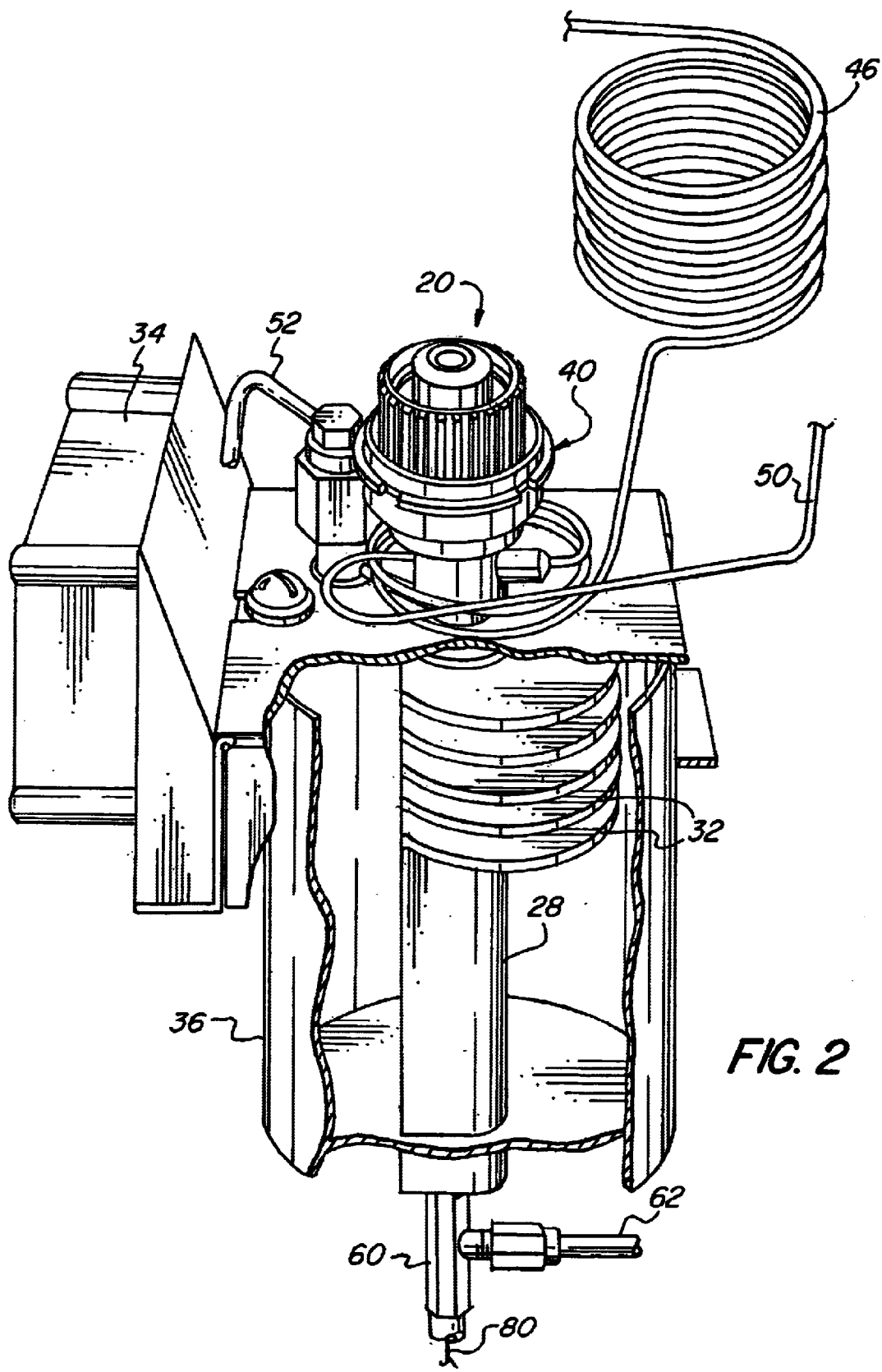
FIG. 2 is an isometric view of a chromatographic injector and a column isolating accessory connected to the bottom of the injector for use with the chromatographic sampling system of FIG. 1.
Figure 3:
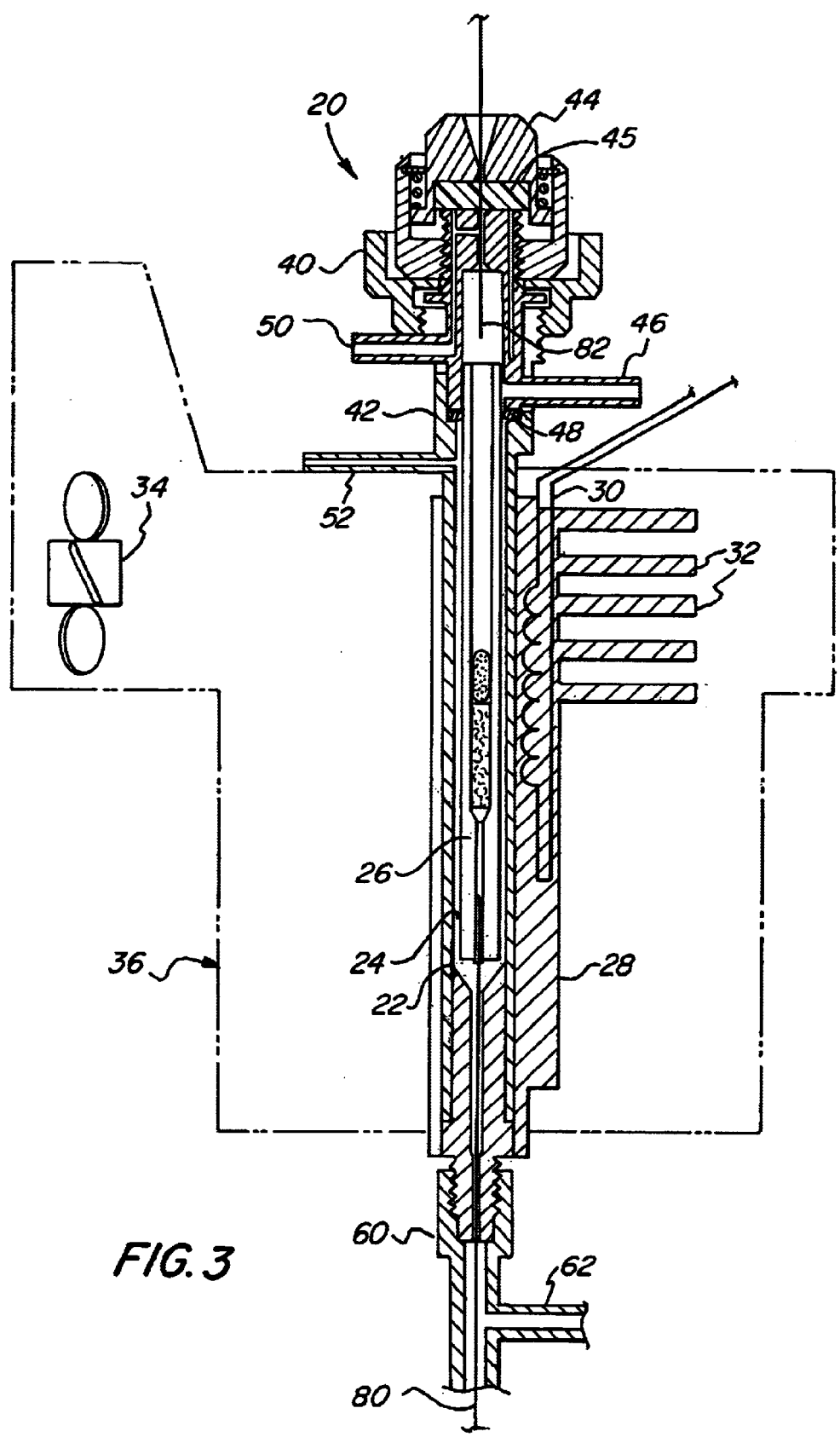
FIG. 3 is an exposed side view of the chromatographic injector and column isolating accessory of FIG. 2.
Figure 4:
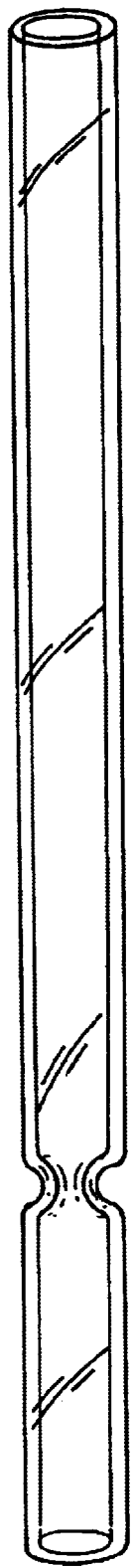
FIG. 4 is a perspective view of a tube used as a liner inside chromatographic injectors known in the prior art.

The basic components of one embodiment of the injector 20, an example of which is the Programmed-Temperature Split/Splitless Inlet System (PSS) Injector manufactured by PerkinElmer Instruments LLC, are illustrated in FIGS. 2 through 3. A metal sleeve 22 creates a chamber 24 in which a removable tube 26 that serves as the "liner" of the injector 20 is inserted. The sleeve 22 is located inside a heater block 28, which is governed by a heating element 30, for heating the chamber 24, including the liner 26. The heater block 28 is provided with cooling fins 32, and a fan 34 may be coupled to a housing 36 for subsequently cooling the chamber 24 and liner 26.

Figure 5:
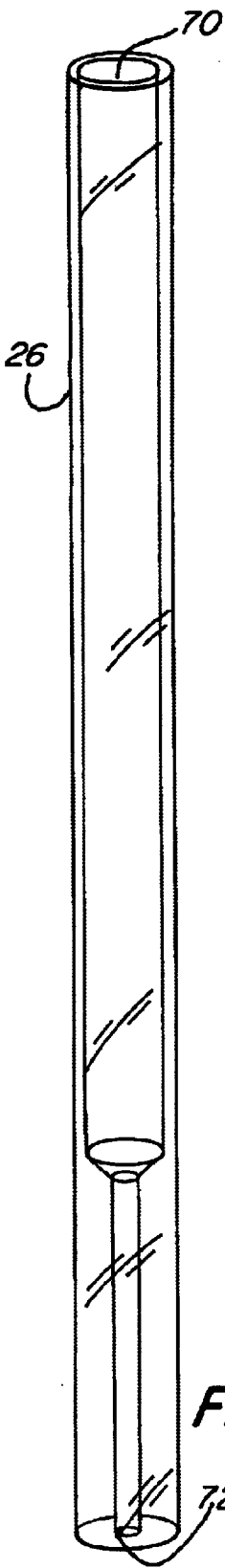
FIG. 5 is a perspective view of an empty tube used as a liner inside the chromatographic injector of FIG. 3.
Figure 6:
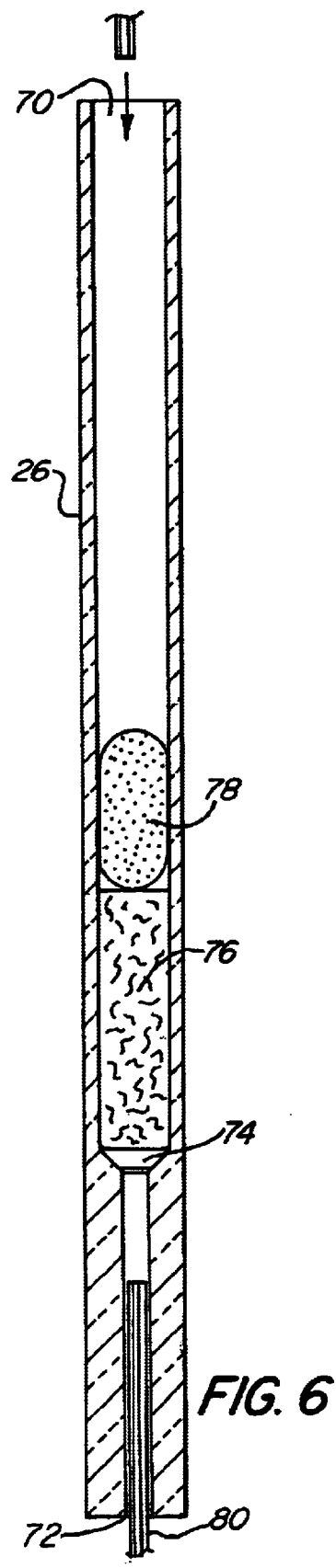
FIG. 6 is a side view of the tube of FIG. 5 containing an adsorbent.
Figure 7:
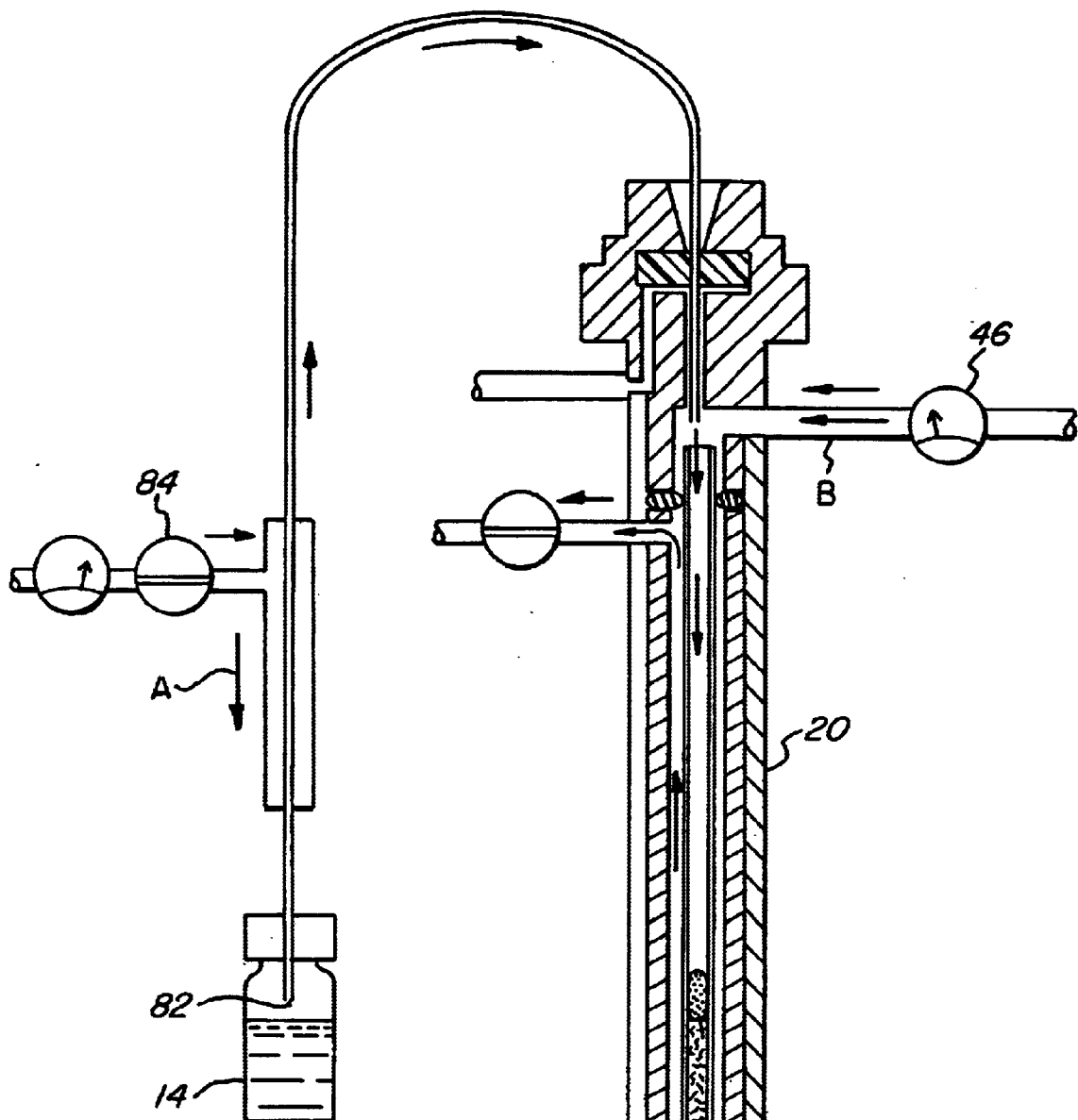
FIG. 7 is an exposed side view of the gas chromatographic system of FIG. 1 during the vial pressurization stage.

Referring to FIGS. 5 through 6, the main features and components of the liner 26 are illustrated. Preferably, the liner 26 is glass. The liner 26 has an inlet 70 located at its top and an outlet 72 located at its bottom. The outlet 72 is restricted, such that the bottom of the liner 26 has an inner diameter smaller than that of the top. A glass disk 74 rests at the top of the restricted bottom of the liner. Above the disk 74, the liner is packed with an adsorbent material 76 capable of adsorbing analytes. Preferably, the adsorbent 76 is hydrophobic. One such adsorbent is graphitized carbon black, such as Carbopack B, manufactured by Supelco. The restricted outlet 72 serves the dual purpose of firmly retaining the adsorbent 76 and significantly reducing the dead volume between the adsorbent 76 and the column 80. Preferably, a glass/quartz wool plug 78 is located above the adsorbent 76 both to facilitate mixing of the sample vapor and the carrier gas and to serve as a surface on which nonvolatile residues from the sample vapor are deposited, thereby permitting easier cleaning of the liner 26. As shown in FIG. 6, the column 80 may be inserted directly into the bottom of the liner 26.

Referring again to FIGS. 2 through 3, a threaded collar 40 secures a septum assembly 42 to the housing 36 at the top of the metal sleeve 22. A septum cap 44 secures a septum 45 to the top of the septum assembly 42, through which septum a microsyringe 82 may inject the sample.

The septum assembly 42 has a main carrier gas inlet 46, the pressure of which can be regulated, which is located above, and separated from the chamber 24 by, an internal seal 48, such as an o-ring. Additionally, septum assembly 42 has a septum purge outlet 50. The septum assembly mechanically defines the path of the septum purge flow to prevent cross contamination with the sample flow path.

Preferably, a "split" vent 52, for splitting the gas mixture, is located below the internal seal 48 and is in fluid communication with the chamber 24.

Preferably, a column isolating accessory 60, such as the PreVent™ System manufactured by PerkinElmer Instruments, LLC, is interposed between the bottom of the injector 20 and the chromatographic column 80. The accessory 60 has an auxiliary carrier gas inlet 62, the pressure of which can be regulated. Additionally, the accessory may have a restrictor tubing (not shown) which is inserted into the bottom of the liner 26 and the top of the column 80 when the accessory is coupled to the bottom of the injector 20.

Operation of the above described gas chromatographic system 10 is illustrated stepwise in FIGS. 7–11. Beginning in FIG. 7, a sampling needle 82 descends into a vial 14. A headspace sampler carrier gas inlet 84 is open to allow carrier gas to pressurize the vial 14 (indicated by arrows A). The main carrier gas inlet 46 is open and set at a pressure appropriate to introduce carrier gas into the injector 20 (indicated by arrows B), and the auxiliary carrier gas inlet 62 is open and set at a slightly lower pressure than the main carrier gas inlet 46 in order to introduce carrier gas into the injector 20 to isolate the chromatographic column 80 from the injector 20 (indicated by arrows C).

Figure 8:
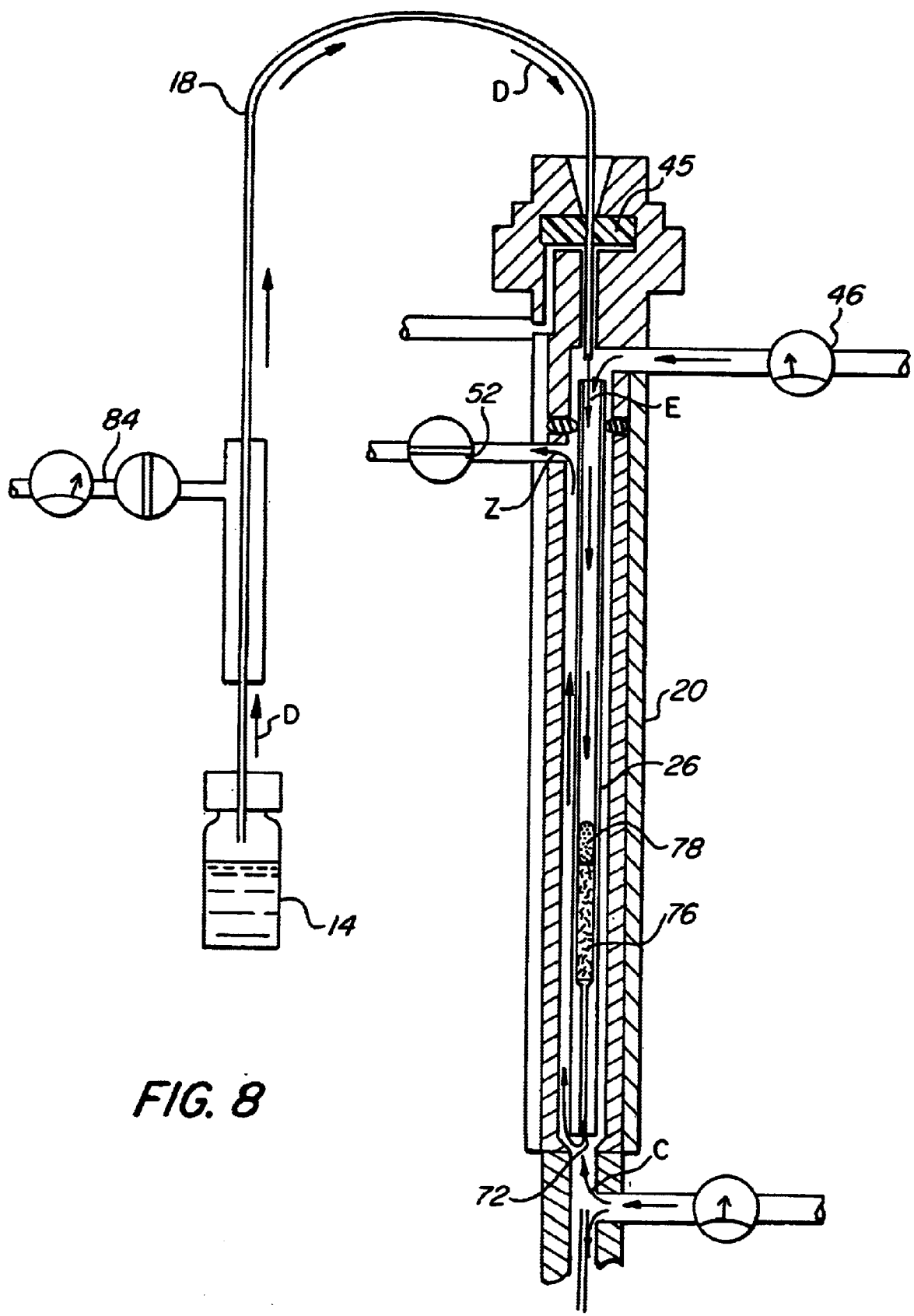
FIG. 8 is an exposed side view of the gas chromatographic system of FIG. 1 during the analyte adsorption stage.

Referring to FIG. 8, the headspace sampler carrier gas inlet 84 is closed, and headspace vapor elutes from the vial 14, down the transfer line 18, through the septum 45, into the injector 20, and into the liner 26 (indicated by arrows D). Carrier gas entering the injector from the main carrier gas inlet 46 mixes with the sample vapor, which mixing is further facilitated by the glass/quartz wool plug 78, and helps to carry the sample vapor through the adsorbent 76 and out the restricted outlet 72 (indicated by arrows E), at which point it mixes with carrier gas entering the injector 20 from auxiliary carrier gas inlet 62 (indicated by arrows C), and out the split vent 52 (indicated by arrows Z).

Referring to FIG. 9, the sampling needle 82 is removed from the vial 14 and the headspace sampler carrier gas inlet 84 is re-opened. The carrier gas supplied by the inlet 84 and the main carrier gas inlet 46 flow through the adsorbent 76 and dry purge the water therefrom (indicated by arrows F). Because the auxiliary carrier gas inlet 62 is still set at a pressure appropriate to isolate the chromatographic column 80 (indicated by arrows C), the water and other unwanted substances that exit the restricted outlet 72 are carried along the outside of the liner 26 and out the split vent 52 (indicated by arrows G). A small additional flow passes over the exposed surface of the septum 45, sweeping volatile contaminants away from the main carrier gas flow, and passes through the septum purge outlet 50 (indicated by arrows H).

Figure 10:
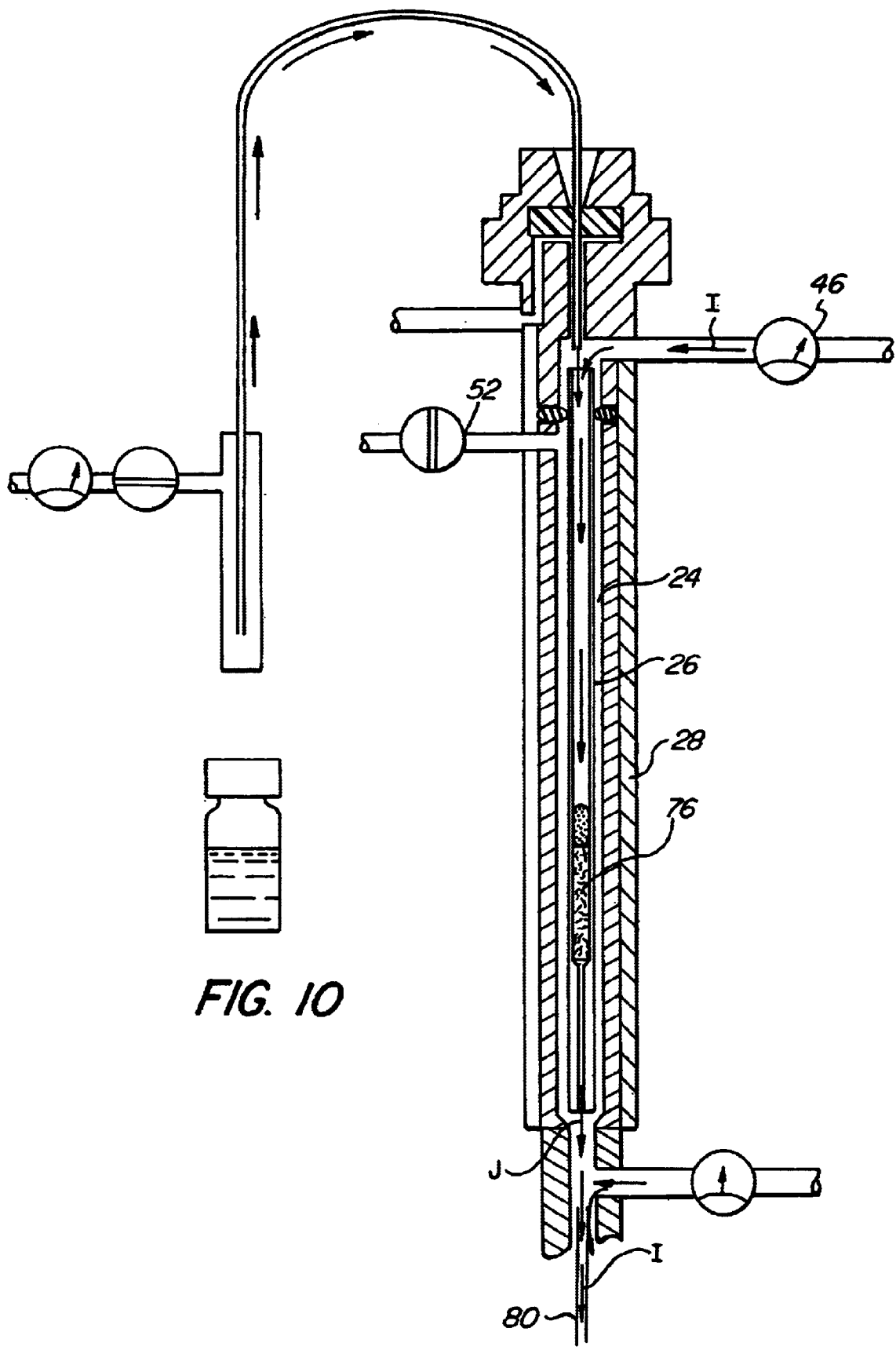
FIG. 10 is an exposed side view of the gas chromatographic system of FIG. 1 during the analyte desorption stage

Referring to FIG. 10, after the water has been removed, the split vent 52 is closed and the pressure of the main carrier gas inlet 46 is increased to permit flow into the column 80 (indicated by arrows I). The chamber 24, including the liner 26, is heated with the heater block 28 so that the analytes adsorbed by the adsorbent 76 are desorbed into the column 80 (indicated by arrows J).

Figure 11:
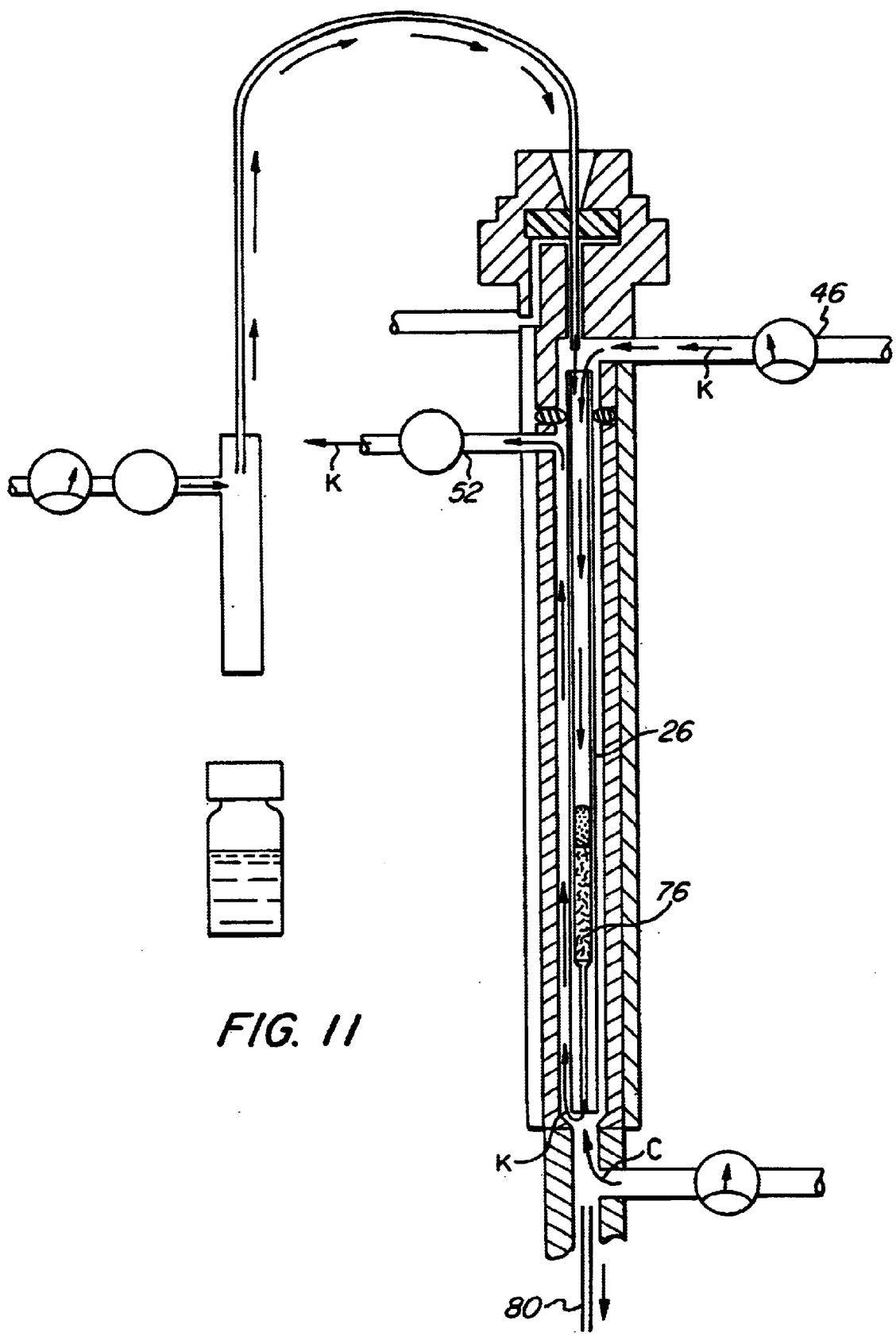
FIG. 11 is an exposed side view of a gas chromatographic system of FIG. 1 during the cleanup stage.

Referring to FIG. 11, after the analytes have been transferred to the column 80, the pressure of the main carrier gas inlet 46 is decreased to again allow the carrier gas introduced into the injector 20 by the auxiliary carrier gas inlet 62 to isolate the column 80 from the injector 20 (indicated by arrows C). The liner 26 is further heated to drive any remaining unwanted less volatile residue off of the adsorbent 76 and out through the split vent 52 (indicated by arrows K).

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of pre-concentrating analytes in a gas chromatographic system including a chromatographic column coupled to a chromatographic injector, which injector has a main carrier gas inlet, the pressure of which can be regulated, an auxiliary carrier gas inlet, the pressure of which can be regulated, a liner, which liner has an inlet and an outlet, wherein the inner diameter of the outlet is smaller than the inner diameter of the inlet, and an adsorbent disposed inside the liner, said method comprising the steps of:

opening the vent and setting the pressures of the main carrier gas inlet and the auxiliary carrier gas inlet such that the column is isolated from substances flowing through the liner;

introducing a sample mixture into the injector, such that the mixture flows into the liner, passes through the adsorbent, which adsorbs the analytes, and is vented from the injector;

closing the vent and setting the pressures of the main carrier gas inlet and the auxiliary carrier gas inlet such that the column is no longer isolated from substances flowing through the injector; and desorbing the analytes adsorbed by the adsorbent into the column.

2. The method of claim 1, further comprising the step of introducing additional carrier gas into the injector, such that the gas flows into the liner, passes through the adsorbent, thereby dry purging moisture therefrom, and is vented from the injector, which step takes place after the sample mixture is vented from the injector but before the vent is closed and the pressures of the inlets are set such that the column is no longer isolated.

3. The method of claim 1, wherein the step of desorbing the analytes includes heating the injector.

4. The method of claim 3, further comprising the steps of:

opening the vent and setting the pressures of the main carrier gas inlet and the auxiliary carrier gas inlet such that the column is again isolated from substances flowing through the liner; and further heating the liner such that any remaining unwanted less volatile residue is driven off of the adsorbent and vented from the injector.

5. The method of claim 1, wherein the chromatographic system further includes a headspace sampler, and the sample mixture is introduced into the injector via carrier gas supplied from the headspace sampler.

6. A method of pre-concentrating analytes in a gas chromatographic system including a chromatographic column coupled to a tube, which tube has an inlet and an outlet, wherein the inner diameter of the outlet is smaller than the inner diameter of the inlet, and an adsorbent disposed inside the tube, comprising the steps of:

introducing a sample mixture into the tube, such that the mixture passes through the adsorbent, which adsorbs the analytes, and is vented from the chromatographic system; and desorbing the analytes adsorbed by the adsorbent into the column.

7. The method of claim 6, further comprising the step of introducing additional carrier gas into the tube, such that the gas passes through the adsorbent, thereby dry purging moisture therefrom, and is vented from the chromatographic system, which step takes place after the sample mixture is vented from the chromatographic system but before the analytes are desorbed into the column.

8. The method of claim 6, wherein the step of desorbing the analytes includes heating the tube.

9. The method of claim 8, further comprising the steps of further heating the tube such that any remaining unwanted less volatile residue is driven off of the adsorbent and vented from the chromatographic system.

10. The method of claim 6, wherein the chromatographic system further includes a headspace sampler, and the sample mixture is introduced into the tube via carrier gas supplied from the headspace sampler.

11. An analyte pre-concentrator for use with a chromatographic column coupled thereto, comprising:
   a housing;
   a tube disposed inside said housing, said tube having an inlet and an outlet, wherein the inner diameter of the outlet is smaller than the inner diameter of the inlet; and
   an adsorbent disposed inside said tube;
   wherein said adsorbent adsorbs analytes when carrier gas carrying a sample mixture containing the analytes flows through said adsorbent before the carrier gas carrying the sample mixture is vented from said housing and while the chromatographic column coupled to said housing is isolated therefrom; and
   wherein said adsorbent desorbs the analytes into the chromatographic column when venting of the carrier gas carrying the sample mixture has ceased and the column is no longer isolated.

12. An analyte pre-concentrator as claimed in claim 11, further comprising a heating element disposed in said housing for controlling the temperature of said tube.

13. An analyte pre-concentrator as claimed in claim 11, wherein said adsorbent is hydrophobic.

14. An analyte pre-concentrator as claimed in claim 13, wherein said adsorbent is graphitized carbon black.

15. An analyte pre-concentrator as claimed in claim 11, wherein:
   said housing comprises a chromatographic injector; and
   said tube comprises a liner disposed inside said injector.

16. An analyte pre-concentrator as claimed in claim 11, further comprising a headspace sampler.

17. An analyte pre-concentrator as claimed in claim 16, wherein said housing is said headspace sampler.

18. An analyte pre-concentrator as claimed in claim 11, further comprising:
   a first fluid pathway in which the sample mixture containing the analytes mixes with carrier gas, flows through said adsorbent, which adsorbs the analytes, and is vented from said housing while the chromatographic column coupled to said housing is isolated therefrom; and
   a second fluid pathway in which the analytes adsorbed by said adsorbent are desorbed into the column.

19. An analyte pre-concentrator as claimed in claim 11, wherein said housing has a vent in fluid communication with the outlet of said tube, through which vent moisture can be vented from said housing.

20. An analyte pre-concentrator as claimed in claim 19, further comprising a column isolating accessory coupled to said housing, with which accessory chromatographic columns coupled to said accessory are isolated from substances flowing through said housing.

21. An analyte pre-concentrator as claimed in claim 20, wherein:

said housing has a sample mixture inlet by which the sample mixture is introduced into said housing, into said tube, through said adsorbent, and out said vent;
said housing has a main carrier gas inlet in fluid communication with the inlet of said tube, by which main carrier gas inlet carrier gas is introduced into said tube;
said column isolating accessory has an auxiliary carrier gas inlet in fluid communication with the outlet of said tube, by which auxiliary carrier gas inlet carrier gas is introduced into said housing to isolate chromatographic columns coupled to said accessory; and
the pressures of the main carrier gas inlet and the auxiliary carrier gas inlet are regulatable to introduce carrier gas into the inlet of said tube and isolate the column while the sample mixture is introduced into said housing, while the sample mixture flows through said adsorbent and out said vent, and while additional carrier gas dry purges said adsorbent and flows out said vent, and are further regulatable to introduce carrier gas into said tube and permit flow into the column while the adsorbed analytes are desorbed into the column.

22. An analyte pre-concentrator for use with a chromatographic column coupled thereto, comprising:
   a housing having a vent;
   a tube disposed inside said housing, said tube having an inlet and an outlet, wherein the inner diameter of the outlet is smaller than the inner diameter of the inlet;
   an adsorbent disposed inside said tube;
   a first fluid pathway defined when the vent is open and the chromatographic column coupled to said housing is isolated therefrom, in which a sample mixture containing analytes mixes with carrier gas, flows through said adsorbent, which adsorbs the analytes, and is vented from said housing; and
   a second fluid pathway defined when the vent is closed and the chromatographic column coupled to said housing is unisolated therefrom, in which the analytes adsorbed by said adsorbent are desorbed into the column.

23. An analyte pre-concentrator as claimed in claim 22, further comprising a heating element disposed in said housing for controlling the temperature of said tube.

24. An analyte pre-concentrator as claimed in claim 22, wherein said adsorbent is hydrophobic.

25. An analyte pre-concentrator as claimed in claim 24, wherein said adsorbent is graphitized carbon black.

26. An analyte pre-concentrator as claimed in claim 22, wherein:
   said housing comprises a chromatographic injector; and
   said tube comprises a liner disposed inside said injector.

27. An analyte pre-concentrator as claimed in claim 22, further comprising a headspace sampler.

28. An analyte pre-concentrator as claimed in claim 27, wherein said housing is said headspace sampler.

29. An analyte pre-concentrator as claimed in claim 22, further comprising a column isolating accessory coupled to said housing, with which accessory chromatographic columns coupled to said accessory are isolated from substances flowing through said housing.

30. An analyte pre-concentrator as claimed in claim 29, wherein;
   said housing has a sample mixture inlet by which the sample mixture is introduced into said housing, into said tube, through said adsorbent, and out said vent;
   said housing has a main carrier gas inlet in fluid communication with the inlet of said tube, by which main carrier gas inlet carrier gas is introduced into said tube;

said column isolating accessory has an auxiliary carrier gas inlet in fluid communication with the outlet of said tube, by which auxiliary carrier gas inlet carrier gas is introduced into said housing to isolate chromatographic columns coupled to said accessory; and the pressures of the main carrier gas inlet and the auxiliary carrier gas inlet are regulatable to introduce carrier gas into the inlet of said tube and isolate the column while the sample mixture is introduced into said housing, while the sample mixture flows through said adsorbent and out said vent, and while additional carrier gas dry purges said adsorbent and flows out said vent, and are further regulatable to introduce carrier gas into said tube and permit flow into the column while the adsorbed analytes are desorbed into the column.

31. An analyte pre-concentrator for use with a chromatographic column coupled thereto, comprising:

a housing having a sample mixture inlet, a main carrier gas inlet, and a vent;

a tube disposed inside said housing, said tube having an inlet and an outlet, wherein the inner diameter of the outlet is smaller than the inner diameter of the inlet;

an adsorbent disposed inside said tube; and a column isolating accessory coupled to said housing having an auxiliary carrier gas inlet;

wherein the sample mixture inlet introduces a sample mixture into said housing, into said tube, through said adsorbent, and out said vent;

wherein the main carrier gas inlet introduces carrier gas into said tube;

wherein the auxiliary carrier gas inlet introduces carrier gas into said housing to isolate chromatographic columns coupled to said accessory; and the pressures of the main carrier gas inlet and the auxiliary carrier gas inlet are regulatable to introduce carrier gas into the inlet of said tube and isolate the column while the sample mixture is introduced into said housing, while the sample mixture flows through said adsorbent and out said vent, and while additional carrier gas dry purges said adsorbent and flows out said vent, and are further regulatable to introduce carrier gas into said tube and permit flow into the column while the adsorbed analytes are desorbed into the column.

32. An analyte pre-concentrator as claimed in claim 31, further comprising a heating element disposed in said housing for controlling the temperature of said tube.

33. An analyte pre-concentrator as claimed in claim 31, wherein said adsorbent is hydrophobic.

34. An analyte pre-concentrator as claimed in claim 33, wherein said adsorbent is graphitized carbon black.

35. An analyte pre-concentrator as claimed in claim 31, wherein:

said housing comprises a chromatographic injector; and said tube comprises a liner disposed inside said injector.

36. An analyte pre-concentrator as claimed in claim 31, further comprising a headspace sampler.

37. An analyte pre-concentrator as claimed in claim 36, wherein said housing is said headspace sampler.

* * * * *